United States Patent [19]

Baylink et al.

[11] Patent Number: 5,693,754
[45] Date of Patent: Dec. 2, 1997

[54] INHIBITORY BINDING PROTEIN FOR INSULIN-LIKE GROWTH FACTORS

[75] Inventors: David J. Baylink; Subburaman Mohan, both of Redlands, Calif.

[73] Assignee: Boehringer Mannheim GmbH, Mannheim, Germany

[21] Appl. No.: 966,121

[22] Filed: Oct. 22, 1992

Related U.S. Application Data

[63] Continuation of Ser. No. 548,388, Jul. 3, 1990, abandoned.
[51] Int. Cl.$^6$ .................... C07K 14/435; C07K 14/65; G01N 33/566
[52] U.S. Cl. .................... 530/350; 530/395; 530/399; 435/7.1; 435/7.21
[58] Field of Search .................... 530/399, 387.1, 530/350, 395; 514/8, 2, 12; 435/7.1, 7.21

[56] References Cited

PUBLICATIONS

Bell, et al., Nature 310: 775–777 (1984).
Canalis et al., J. Clin. Invest. 66: 709–719 (1980).
Mohan et al., Biochim. Biophys. Acta. 966: 4–55 (1988).
Arteaga et al., J. Clin. Invest. 84: 1418–1423 (1989).
El–Badry et al., J. Clin. Invest. 84: 829–839 (1989).
Forbes et al., Biochem. Biophys. Res. Commun. 157: 196–202 (1988).
Povoa et al., Eur. J. Biochem. 144: 199–204 (1984).
Koistinen et al., Endocrinology 118: 1375–1378 (1986).
Bell and Keyte, Endocrinology 123: 1202–1204 (1988).
Povoa et al., Biochem. Biophys. Res. Commun. 128: 1071–1078 (1985).
Brinkman et al., EMBO J. 7: 2417–2423 (1988).
Lee et al., Mol. Endocrinol. 2: 404–411 (1988).
Brewer et al., Biochem. Biophys. Res. Commun. 152: 1289–1297 (1988).
Julkumen et al., FEBS Lett. 236: 295–302 (1988).
Mottola et al., J. Biol. Chem. 261: 11180–11186 (1986).
Szabo et al., Biochem. Biophys. Res. Commun. 151: 207–214 (1988).
Brown et al., J. Biol. Chem. 264: 5148–5154 (1989).
Baxter et al., J. Biol. Chem. 264: 11843–11848 (1989).
Baxter and Martin, Proc. Natl. Acad. Sci. USA 86: 6898–6902 (1989).
Wood et al., Mol. Endocrinol. 2: 1176–1185 (1989).
Martin et al., J. Biol. Chem. 265: 4124–4130 (1990).
Mohan et al., Proc. Natl. Acad. Sci. USA 86: 8338–8342 (1989).

*Primary Examiner*—Stephen Walsh
*Assistant Examiner*—Daryl A. Basham
*Attorney, Agent, or Firm*—Felfe & Lynch

[57] ABSTRACT

The invention provides homogeneous compositions of a binding protein for insulin-like growth factors (IGFs) I and II, which binding protein inhibits the proliferative effects of IGF-I and IGF-II upon bone cells. The homogeneous protein of the invention is therefore known as inhibitory IGF binding protein, or In-IGF-BP. The invention also provides cloned nucleic acid sequences encoding In-IGF-BP, artificial expression systems for In-IGF-BP and host cells which produce useful quantities of In-IGF-BP. The invention further provides clinical diagnostic assays for IGFs, therapeutic treatments for IGF-responsive tumors, and means for modulating IGF activity upon bone cells.

3 Claims, 5 Drawing Sheets

FIG. 1A

```
                                            Met Leu Pro Leu Cys Leu Val
CCC GCG CCC AGT CCT CGG GCG GTC             ATG CTG CCC CTC TGC CTC GTG    -42
                                                                      1
Ala Ala Leu Leu Ala Ala Gly Pro Gly Pro Ser leu Gly Pro Ser leu Gly Asp
GCC GCC CTG CTG GCC GCC GGG CCC GGG CCG AGC CTG GGG CCG AGC CTG GGC GAC      3

Glu Ala Ile His Cys Pro Pro Cys Ser Glu Glu Lys Leu Ala Arg
GAA GCC ATC CAC TGC CCC CCG TGC TCC GAG GAG AAG CTG GCG CGC                 48
                                                              1

Cys Arg Pro Val Gly Cys Glu Glu Leu Val Arg Glu Ala Gly
GGC CGC CCC GTG GGC TGC GAG GAG CTG GTG CGA GAG GCG GCG                     93

Cys Gly Cys Cys Ala Thr Cys Ala Leu Gly Leu Gly Met Pro Cys
TGC GGC TGT GCC ACT TGC GCC CTG GGC CTT GGG ATG CCC TGC                    138
            50

Gly Val Tyr Thr Pro Arg Cys Gly Ser Gly Leu Arg Cys Try Pro
GGG GTG TAC ACC CCC CGT TGC GGC TCG GGC CTG CGC TGC TAC CCG                183

Pro Arg Gly Val Glu Lys Pro Leu His Thr Leu Met His Gly Gln
CCC CGA GGG GTG GAG AAG CCC CTG CAC ACA CTG ATG CAC GGG GAA                228

Gly Val Cys Met Glu Leu Ala Glu Ile Gln Glu Ser
GGC GTG TGC ATG GAG CTG GCG GAG ATC GAG GCC ATC CAG GAA AGC                273
                                    100
```

FIG. 1B

```
Leu Gln Pro Ser Asp Lys Asp Glu Gly Asp His Pro Asn Asn Ser
CTG CAG CCC TCT GAC AAG GAC GAG GGT GAC CAC CCC AAC AAC AGC    318

Phe Ser Pro Cys Ser Ala His Asp Arg Arg Cys Leu Gln Lys His
TTC AGC CCC TGT AGC GCC CAT GAC CGC AGG TGC CTG AAG CAC        363

Phe Ala Lys Ile Arg Asp Arg Ser Thr Ser Gly Gly Lys Met Lys
TTC GCC AAA ATT CGA GAC CGG AGC ACC AGT GGG GGG AAG ATG AAG    408
                                                        150
Val Asn Gly Ala Pro Arg Glu Asp Ala Arg Pro Val Pro Gln Gly
GTC AAT GGG GCG CCC CGG GAG GAT GCC CGG CCT GTG CCC CAG GGC    453

Ser Cys Gln Ser Glu Leu His Arg Ala Leu Glu Arg Leu Ala Ala
TCC TGC CAG AGC GAG CTG CAC CGG GCG CTG GAG CGG CTG GCC GCT    498

Ser Gln Ser Arg Thr His Glu Asp Leu Tyr Phe Ile Pro Ile Pro
TCA CAG AGC CGC ACC CAC GAG GAC CTC TAC TTC ATC CCC ATC CCC    543

Asn Cys Asp Arg Asn Gly Asn Phe His Pro Lys Cys Trp Cys Val Asp Arg Lys
AAC TGC GAC CGC AAC GGC AAC TTC CAC CCC AAG TGT TGG TGT GTG GAC CGG AAG   588

Ala Leu Asp Gly Gln Arg Gly Lys Cys Trp Cys Val Asp Arg Lys
GCT CTG GAT GGG CAG CGT GGC AAG TGT TGG TGT GTG GAC CGG AAG    633

Thr Gly Val Lys Leu Pro Gly Gly Leu Glu Pro Lys Gly Glu Leu
ACG GGG GTG AAG CTT CCG GGG CTG GAG CCA AAG GGG GAG CTG        678

Asp Cys His Gln Leu Ala Asp Ser Phe Arg Glu ***
GAC TGC CAC CAG CTG GCT GAC AGC TTT CGA GAG TGA GGC CTG CCA    723
                                     237
```

FIG. 4

INHIBITORY BINDING PROTEIN FOR INSULIN-LIKE GROWTH FACTORS

This is a continuation of application Ser. No. 07/548,388, filed Jul. 3, 1990, now abandoned.

BACKGROUND OF THE INVENTION

1. Field of the Invention

The invention relates to bone metabolism, and more particularly to bone metabolic processes which are mediated by the insulin-like growth factors I and II (IGF-I and IGF-II). Specifically, the invention relates to proteins which inhibit the effect of IGF-I and IGF-II upon cellular proliferation, and especially upon bone cell proliferation as well as to nucleic acids encoding these proteins. Such proteins according to the invention specifically bind IGF-I and IGF-II and modulate IGF function. Thus such proteins could be used in scientific studies to determine what structural features of IGF-I or IGF-II relate to their respective functions. They may also be used to assess IGF concentrations in clinical samples or to inhibit proliferation of bone tumor or other tumor cells which are induced to proliferate by IGF-I or IGF-II.

2. Summary of Related Art

Insulin-like growth factors (IGF) I and II are somatomedins which stimulate cell proliferation and play a critical physiologic regulatory role in bone metabolism. Numerous references describe the structure and function of these proteins.

Bell, et al., Nature 310:775–777 (1984) discloses that IGF-I and IGF-II are single chain serum proteins of 70 and 67 amino acids, respectively, and reports the growth hormone-dependence of IGF-I as well as the molecular cloning of IGF-II.

Although structurally similar, IGF-I and IGF-II play very different roles in human bone metabolism. IGF-I mediates bone growth in a growth hormone-dependent fashion, whereas IGF-II stimulates bone formation associated with bone turnover in adults.

Canalis et al., J. Clin. Invest. 66:709–719 (1980), discloses the role of IGF-I in the regulation of bone growth.

The role of IGF-II in mediating bone formation associated with bone turnover is disclosed in co-pending U.S. patent application Ser. No. 07/043,628, filed Apr. 28, 1987 (now abandoned). See also Mohan et al., Biochim. Biophys. Acta. 966:4–55 (1988).

Certain tumor cells, such as osteosarcomas, breast cancer cells, neuroblastomas and hepatomas produce IGFs, which in turn induce the proliferation of these tumor cells. See Arteaga et al., J. Clin. Invest. 84:1418–1423 (1989).

In addition, the critical role of IGFs in regulating bone formation is consistent with a causal relationship between aberrant level of IGFs and a variety of bone metabolism disorders, including displasias and osteopenias such as osteoporosis. See El-Badry et al., J. Clin. Invest. 84:829–839 (1989).

Despite reports in the literature relating to the functions of IGF-I and IGF-II, relatively little is known about what specific determinants on these molecules mediate their functions. There is, therefore, a need for agents which specifically bind and modulate the effects of IGF-I and IGF-II. Such agents would be useful in structure-function studies of IGFs, in the assay of IGFs in clinical samples, and in the treatment of tumors which proliferate in response to IGF-I or IGF-II.

Various binding proteins for IGF-I and IGF-II have been reported in the literature. Baxter and Martin, Prog. Growth Factor Res. 1:49–68 (1989) reports that at least three separate, but structurally related groups of binding proteins exist. See also Forbes et al., Biochem. Biophys. Res. Commun. 157:196–202 (1988).

Type I binding protein (IGF-BP I) has been analyzed from several human sources, including amniotic fluid, placental membranes, decidua, and HEP G2 hepatoma cells, and the N-terminal amino acid sequences of these proteins are identical. See Proyon et al., Eur. J. Biochem. 144:199–204 (1984); Koistinan et al., Endocrinology 118:1375–1378 (1986); Bell and Keyta, Endocrinology 123:1202–1204 (1988); Povoa et al., Biochem. Biophys. Res. Commun. 128:1071–1078 (1985).

Recently, the cloning and sequencing of the cDNA for IGF-BP I has been reported. See Brinkman et al., EMBO J. 7:247–2423 (1988); Lee et al., Mol. Endocrinol. 2:404–411 (1988); Brewer et al., Biochem. Biophys. Res. Commun. 152:1289–1297 (1988); Julkumen et al., FEBS Lett. 236:295–302 (1988).

Type II binding proteins (IGF-BP II) have also been analyzed. Mottola et al., J. Biol. Chem. 261:11180–11186 (1986) discloses the presence of IGF-BP II in conditioned medium from rat BRL-3A cells, and Szabo et al., Biochem. Biophys. Res. Commun. 151:207–214 (1988) discloses its presence in conditioned medium from MDBK cells. Brown et al., J. Biol. Chem. 264:5148–5154 (1989) discloses the cloning of a cDNA encoding IGF-BP II.

The type III binding protein (IGF-BP III) is found in serum as a 150 kilodalton ternary complex between IGF-I or IGF-II, an acid labile glycoprotein of about 85 kilodaltons and the IGF-BP III molecule, which is an acid stable glycoprotein of 53 kilodaltons. See Baxter et at., J. Biol. Chem. 264:11843–11848 (1989); Baxter and Martin, Proc. Natl. Acad. Sci. USA 86:6898–6902 (1989). Wood et al., Mol. Endocrinol. 2:1176–1185 (1989), discloses the cloning and sequencing of the cDNA encoding IGF-BP III.

Martin et al., J. Biol. Chem. 265:4124–4130 (1990) discloses the purification of an IGF binding protein (TFBP) from culture medium conditioned by AG 2804 transformed fibroblast cells, which exhibits strong preferential binding for IGF-II relative to IGF-I.

Thus the related art establishes that a variety of IGF binding proteins are produced by different sources and that these proteins exhibit disparate binding properties and presumably functions. Differences in binding properties suggest that different functional determinants on IGF-I and IGF-II are likely to be recognized by different IGF-BPs. In order to understand how these various determinants relate to IGF-I and IGF-II function in bone metabolism, there is a need to find IGF-BPs which are produced by bone cells and which thus present a strong likelihood of inolvement in regulating bone metabolism. Such IGF-BPs are also needed for purposes of clinical assays relating to the diagnosis of defects in bone metabolism. IGF-BPs which inhibit the IGF-dependent growth of bone neoplasia are also needed for diagnostic and therapeutic applications to such neoplasias.

BRIEF SUMMARY OF THE INVENTION

The present invention relates to means for scientific studies, clinical diagnosis and therapeutic treatments for bone metabolic disorders and neoplasias related to IGF-mediated bone formation or cell proliferation. More particularly, the invention relates to a novel purified binding protein for IGF-I and IGF-II. This protein is known as inhibitory IGF binding protein (In-IGF-BP). The invention provides, for the first time, an agent which can inhibit IGF-mediated cell proliferation, inhibit growth of IGF-responsive tumor cells, and enhance or retard cellular differentiation, as well as bind IGFs with greater affinity than previously reported binding proteins. The purified protein of the invention is the major IGF-BP known to be produced by bone cells. The characteristics of this purified protein thus make it an ideal agent for scientific studies of the structure-function relationships of determinants of IGFs which are involved in regulation of bone metabolism, as well as for clinical evaluation of IGF levels in samples from patients with bone metabolism disorders. The capacity of the purified protein of the invention to inhibit proliferation of IGF-responsive tumor cells make it a useful agent for the assessment of IGF-responsiveness of a patient's cancer, as well as for therapeutic treatment of IGF-responsive tumors.

The invention also provides the complete nucleotide sequence encoding in-IGF-BP, thus enabling further scientific studies and the production of useful quantities of In-IGF-BP for the applications noted above, and allowing further development of improved variants of in-IGF-BP which exhibit superior diagnostic, therapeutic or scientifically useful properties.

DETAILED DESCRIPTION OF THE SPECIFIC EMBODIMENTS

We have described the isolation of In-IGF-BP in a recent article, Mohan et al., Proc. Natl. Acad. Sci. USA 86:8338–8342 (1939) which is hereby incorporated by reference.

In a first aspect, the invention provides a purified protein which binds specifically to IGF-I and IGF-II. The protein may be purified to apparent homogeneity from culture medium conditioned by normal human bone cells, by TE89 human osteosarcoma cells, or by host cells transfected by and expressing the DNA sequence encoding in-IGF-BP. Purification has been achieved by either of two procedures, starting with clarified culture medium. In the first procedure purification is accomplished by gel filtration, followed by ion exchange on FPLC, C4 reverse phase on HPLC, and finally by a CN reverse phase chromatography step on HPLC. The second procedure utilizes two steps: affinity chromatography on a column with bound IGF-I and reverse phase chromatography on HPLC. Apparent homogeneity of the purified protein from either procedure is demonstrated by its migration as a single band on SDS-PAGE and by the production of a single amino acid sequence signal on N-terminal analysis. Specific binding of IGF-I and IGF-II is demonstrated by a polyethylene glycol (PEG) precipitation assay, by a competition assay for specific receptor binding of IGFs and by chemical cross-linking of IGF and In-IGF-BP. In this aspect the invention provides a purified protein which is useful in structure-function studies of determinants of IGFs which allow binding to specific receptors as well as to the binding protein. Thus the purified protein of the invention provides a means for examining the important role of IGFs in regulating bone metabolism. Further utility of the purified protein of the invention is disclosed in the descriptions of other aspects of the invention below.

The purified IGF binding protein of the invention is unique and distinct from all previously identified IGF binding proteins. Human IGF-BP I, IGF-BP II and IGF-BP III are characterized by amino acid sequences which have been published and which are distinct from the amino acid sequence of In-IGF-BP. The N-terminal amino acid sequence reported for the IGF binding protein TFBP is also distinct from that of In-IGF-BP. Previously reported IGF-BPs are further distinguished from In-IGF-BP in that they are not the major IGF-BP actually produced by bone cells and differ from IGF-BP in other biochemical characteristics. For example, IGF-BP I is less potent than In-IGF-BP in cell proliferation inhibition, and IGF-BP III, unlike In-IGF-BP, actually may enhance IGF-I mediated cell proliferation in vitro. Both IGF-BP II and TFBP display a marked preference for binding IGF-II relative to IGF-I, also unlike In-IGF-BP.

Figure 1A:
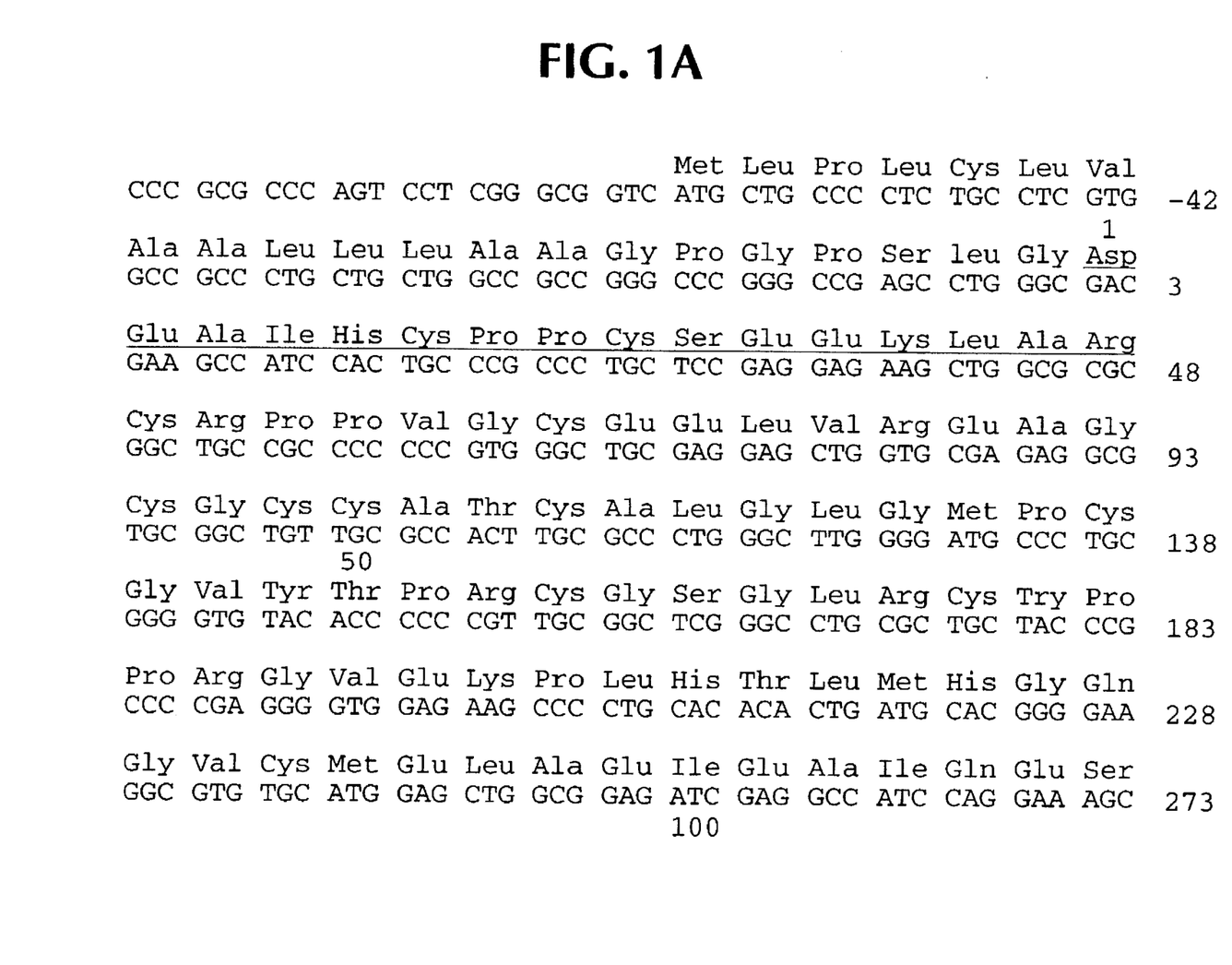
FIG. 1 shows the nucleotide sequence encoding In-IGF-BP and flanking sequences, as well as the deduced amino acid sequence of In-IGF-BP.
Figure 1B:
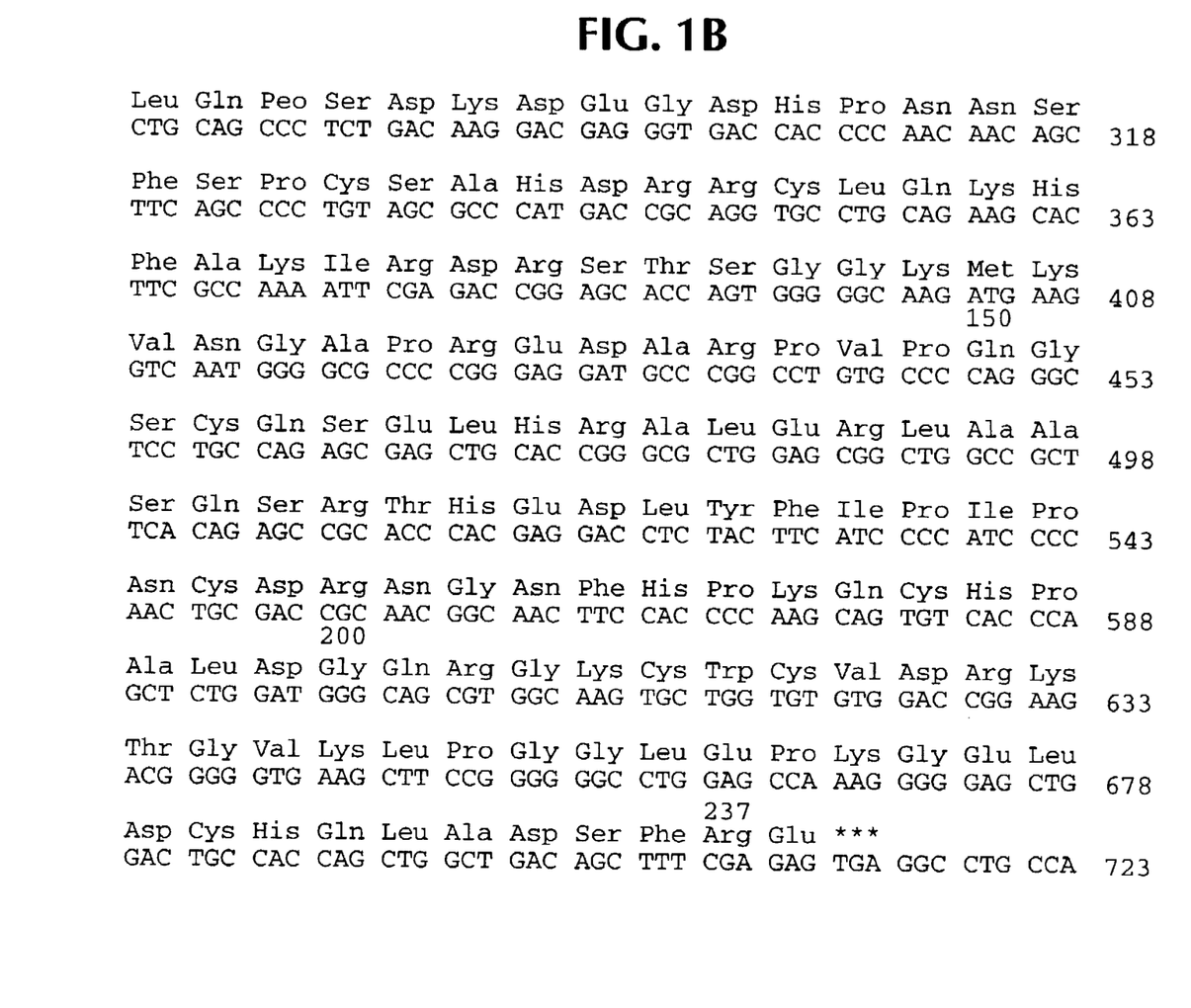

The homogeneous human IGF binding protein of the invention (In-IGF-BP) is characterized by an amino acid sequence identical to, or substantially identical to that shown in FIG. 1. For purposes of the invention, an amino acid sequence substantially identical to that shown in FIG. 1 is understood to mean an amino acid sequence identical to that of FIG. 1 except for the presence of conservative amino acid substitutions or other amino acid substitutions, insertions or deletions which do not materially affect the binding of the substantially identical protein to IGF-I or IGF-II, or otherwise materially alter its function in the applications set forth below.

In a second aspect, the invention provides an agent which is effective in inhibiting bone cell proliferation in response to IGF-I, IGF-II or serum. Chicken bone cells make both IGF-I and IGF-II, which in turn mediate their proliferation. Addition of In-IGF-BP to cultured chicken bone cells in serum-free medium inhibits this proliferation. Exogenously supplied IGF-I or IGF-II increases the proliferative rate of chicken bone cells in serum-free medium. This effect also is inhibited by treatment of chicken bone cells with In-IGF-BP. Finally serum, which contains a variety of proliferation-inducing factors, is the strongest stimulator of bone cell proliferation yet discovered. In-IGF-BP is effective in inhibiting proliferation of chicken bone cells in response to serum. While IGF-BP I has previously been shown to inhibit cell proliferation, the invention provides an agent, In-IGF-BP, which is several-fold more potent than IGF-BP I. Thus the invention provides an agent which is useful for studying the physiological function of IGF-I, IGF-II and other serum growth factors in in vitro biological systems.

In another aspect, the invention provides a reagent for the diagnostic evaluation of IGF-I or IGF-II levels in clinical samples taken from patients suffering from bone metabolism disorders or from bone neoplasia. Purified In-IGF-BP may be used in sensitive, quantitative competition assays using labelled IGF-I or IGF-II. The specificity of binding of IGFs by In-IGF-BP allows the quantitation of IGFs in clinical samples by measuring the displacement of labelled IGF-I or IGF-II from bound In-IGF-BP by the unlabelled IGF-I or IGF-II in the clinical sample. Thus the involvement of aberrant levels of IGF-I or IGF-II in disorders of bone metabolism or the likelihood of IGF-responsiveness of particular tumors can be readily assessed by assay of clinical samples using the purified protein of the invention.

In another aspect, the invention provides a therapeutic agent for the treatment of tumors which proliferate in response to IGFs. Bone tumor cells and other neoplastic cells which proliferate in response to IGFs are inhibited in growth by treatment with In-IGF-BP in vitro, whether the IGF is produced by the neoplastic cells or provided from another source. Thus purified In-IGF-BP provided by the invention may be formulated in a pharmaceutically acceptable carrier or diluent and used to retard tumor growth by localized delivery of such pharmaceutical composition.

In another aspect, the invention provides a readily-manipulatable complete nucleotide sequence encoding In-IGF-BP. A cDNA library was prepared from human osteosarcoma cell RNA and was screened for clones encoding In-IGF-BP using mixed oligonucleotide probing. A full-length clone encoding In-IGF-BP was isolated. This clone, representing the coding sequence for In-IGF-II is useful for scientific studies evaluating the cell and tissue specificity, and hormone responsiveness of expression of In-IGF-BP, which will shed light upon the complex regulatory interactions between IGFs and their binding proteins. It will also be useful in temporal expression studies designed to examine the role of IGFs and IGF-BPs in development. This nucleotide sequence is also useful for studies of the evolutionary relationships between In-IGF-BP and other IGF-BPs.

The clone was also used to make artificial expression systems for In-IGF-BP. As the degeneracy of the genetic code and methods for nucleotide substitution are well known in the art, this aspect of the invention contemplates and fully enables the construction of artificial expression systems comprising a nucleotide sequence encoding In-IGF-BP and containing one or more silent mutations. The artificial expression systems of the invention produce active In-IGF-BP which exhibits activity characteristic of the In-IGF-BP purified from the conditioned medium of osteosarcoma cells or normal human bone cells. As recombinant DNA artificial expression systems, coupled with the purification methods of the invention allow the production of In-IGF-BP in essentially unlimited quantities, the invention provides a means for producing useful quantities of In-IGF-BP for all of the previously mentioned applications, including large-scale diagnostic and therapeutic clinical applications. For purposes of the invention an artificial expression system is defined as a nucleotide sequence encoding functional In-IGF-BP as an independent protein or as part of a fusion protein, coupled with a suitable promoter element which allows the expression of such functional In-IGF-BP in a transformed host cell, wherein such artificial expression system is capable of replication either as an episome or as integrated in a chromosome of the host cell. The artificial expression systems of the invention may be cloned into a plasmid or artificial chromosome, or may be integrated in the chromosome of the host cell, so long as they are not in a state which is naturally occurring. A naturally occurring expression system for In-IGF-BP is understood to mean that DNA sequence encoding In- IGF-BP which is expressed from its native promoter element and which is found in its natural location in its native human chromosome.

The invention further provides host cells which produce In-IGF-BP by virtue of transformation or transfection of such host cells with one or more artificial expression systems for In-IGF-BP. The host cells of the invention may be bacterial, yeast, insect, plant or mammalian cells, so long as such host cells do not naturally produce useful quantities of In-IGF-BP, i.e., so long as the production of useful quantities of In-IGF-BP is due to transfection by or expression of an artificial expression system for In-IGF-BP.

The following examples set forth certain specific embodiments of the invention and are provided to enable those of skill in the art to practice the invention and to illustrate the utility of the invention in certain applications. These examples should not be construed to limit the scope of the invention, which is limited only by the lawful scope of the appended claims.

Example 1

Preparation of Conditioned Medium For Purification of In-IGF-BP

Human bone cells or TE89 human osteosarcoma cells were grown in monolayer cultures in petri dishes or roller bottles in DMEM supplemented with 10% calf serum. Cells were grown to 60–80% confluence, then rinsed twice with serum free DMEM and maintained in serum free medium for collection of conditioned medium. Two day collections of conditioned medium were taken and stored at −20° C. Pooled collections of conditioned medium (5 liters) were centrifuged at 500× g to remove cellular debris. Clarified conditioned medium was acidified with glacial acetic acid (final concentration 1M) to dissociate binding proteins from IGFs. Acidified conditioned medium was concentrated using an AMICON YM5™ membrane.

Example 2

Purification of In-IGF-BP: Scheme 1

Concentrated acidified conditioned medium, prepared according to Example 1, was lyophilized, reconstituted in 2.5 ml of 1M acetic acid and applied to a SEPHADEX G100™ column (2.5×100 cm). Proteins were eluted with 1M acetic acid and 2 ml fractions were collected. Fractions containing IGF-BP activity were pooled and lyophilized. The lyophilized material was reconstituted with 20 mM Tris-HCl, pH 8.0 and applied to an FPLC Mono Q column. Proteins were eluted using a NaCl gradient (0 mM to 500 mM in 60 minutes) and two minute fractions were collected and assayed for IGF-BP activity. Fractions comprising the IGF-BP activity peak were pooled, concentrated and subjected to HPLC reverse phase chromatography in 0.1% TFA using a 4.6×250 mm C4 column (BIORAD RP 304™). Unbound proteins were eluted for 5 minutes with 15% acetonitrile in 0.1% TFA. Bound proteins were eluted using a linear acetonitrile gradient (15–40% in 125 minutes) and 2 minute fractions were collected and assayed for IGF-BP activity. Active fractions were subjected to HPLC reverse phase chromatography in 0.1% TFA using a 3.9×150 mm microbondpak CN column (Waters Corporation, Milford, Mass.) and a 1-propanol gradient (20-0% in 100 minutes) to obtain homogeneous In-IGF-BP.

Example 3

Purification of In-IGF-BP: Scheme 2

Concentrated acidified conditioned medium prepared according to Example 1 was dialyzed against phosphate-buffered saline (PBS), ph 7.4 and applied to an affinity column composed of recombinant human IGF-I coupled to CnBr-activated SEPHAROSE 4B™. Unbound proteins were eluted with PBS, then bound proteins were eluted the 4M guanidine-HCl, pH 7.4. The guanidine-HCl eluate was dialyzed against 0.1% TFA. Homogeneous In-IGF-BP was then obtained using the same HPLC column and linear acetonitrile gradient as described for the penultimate step of Example 2.

Example 4

Assessment of Purity of In-IGF-BP

Figure 2:
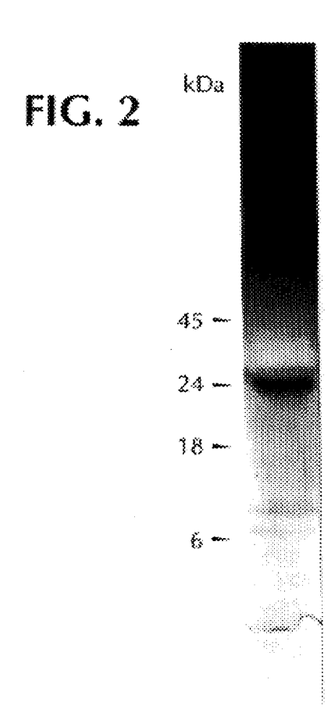
FIG. 2 shows a silver stained polyacrylamide gradient gel lane in which was loaded 0.5 micrograms of homogeneous In-IGF-BP.

To assess the purity of In-IGF-BP isolated according to Examples 2 or 3 above, 0.5 micrograms of purified material at pH 8.8 was applied to a 3–27% polyacrylamide gradient slab gel under reducing conditions. As shown in FIG. 2, a single major protein band at 25 kilodaltons was observed in the silver-stained gel. Further evidence that the material was homogeneous was provided by N-terminal amino acid sequencing which produced a single sequence signal.

Example 5

PEG Precipitation Competitive Binding Assay For In-IGF-BP

Fifty microliters of sample to be assayed for In-IGF-BP was incubated with 25,000–50,000 cpm of $^{125}$I-labelled IGF-I or IGF-II ($^{125}$I-IGF-I or $^{125}$I-IGF-II) for 60 minutes at room temperature in 250 microliters 0.1M HEPES/0.1% bovine serum albumin/0.1% TRITON X-100™/44 mM Na2 CO3/0.02% NAN3, pH 6.0. To this mixture was added 100 microliters of 2% immune serum globulin and 500 microliters of 25% polyethylene glycol (PEG), followed by centrifugation. Under these conditions, the PEG precipitated the larger complex between IGF-I or IGF-II and In-IGF-BP, but did not precipitate unbound IGF-I or IGF-II. The amount of $^{125}$I-IGF in the PEG precipitated was then counted. Non-specific binding was determined by carrying out the assay in the presence of excess unlabelled IGF-I or IGF-II and the amount of $^{125}$I-IGF-I or $^{125}$I-IGF-II precipitated was subtracted from the value obtained above.

Example 6

IGF-II Radioreceptor Assay For In-IGF-BP

Mohan et al., Biochim. Biophys. Acta 966:44–55 (1988), describes a radioreceptor assay for IGF-II using H-55 rat hepatoma cells (which contain abundant IGF-II receptors but no IGF-I receptors) and $^{125}$I-IGF-II. The assay described in that article, which is hereby incorporated by reference, measures concentrations of IGF-II in a sample by assessing the ability of various dilutions of the sample to compete away binding of $^{125}$I-IGF-II to the H-35 cells. The assay was adapted to measure In-IGF-BP by replacing the unlabelled IGF-II sample with the sample to be assayed for In-IGF-BP. The assay was used with a purified In-IGF-BP standard to determine the concentration of In-IGF-BP recovered after each step of the procedures described in Examples 1 and 3 above. The results are shown in Table 1.

TABLE I

| Purification Step | Micrograms/ml In-IGF-BP | Volume in ml | Total Micrograms In-IGF-BP | % Recovery |
|---|---|---|---|---|
| Conditioned Medium | 0.041 | 4890 | 200.5 | 100 |
| Concentrate | 1.28 | 75 | 96.0 | 48 |
| IGF-I Affinity | 1.09 | 50 | 54.5 | 27 |
| HPLC reverse-phase column | 9.22 | 4 | 36.9 | 18 |

Example 7

Use of In-IGF-BP in Chemical Cross-Linking Studies

Figure 3:
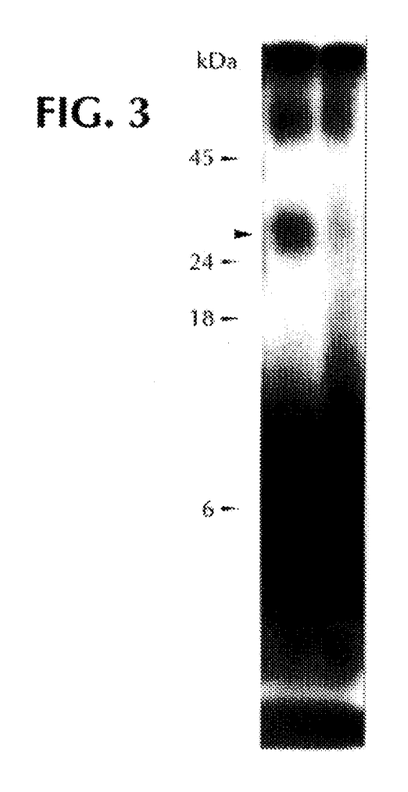
FIG. 3 shows an autoradiograph of an SDS-PAGE on which was loaded the product of coincubation and chemical crosslinking between $^{125}$I-IGF-II and In-IGF-BP in the absence (−) or presence (+) of excess unlabelled competitor IGF-II.

One nanogram of purified In-IGF-BP was incubated with 40,000 cpm of $^{125}$I-IGF-II in the presence or absence of 10 ng unlabelled IGF-II competitor. Binding was performed in 0.1 ml of 50 mM sodium phosphate buffer 0.1% bovine serum albumin, pH 6.5 at room temperature for 60 minutes. Two microliters of 25 mM dissuccinimidyl suberate (freshly prepared in dimethyl sulfoxide) was added and the incubation was allowed to continue for another 20 minutes. One hundred microliters of 2× electrophoresis sample buffer was added and the samples were boiled for 3 minutes. The complex between In-IGF-BP and $^{125}$I-IGF-II was separated from free $^{125}$I-IGF-II by electrophoresis on a 15% SDS-polyacrylamide slab gel. The gel was air dried and exposed to KODAK X-OMAT AR™ film using an intensifying screen for 7 days at –70° C. As shown in FIG. 3, a band was observed at 32 kilodaltons, which is the expected molecular weight for the complex between In-IGF-BP (25 kilodaltons) and IGF-II (7.5 kilodaltons). The specificity of the binding and subsequent cross-linking was demonstrated by the diminished signal of this band when the incubation included excess unlabelled competitor IGF-II. As little is known about the specific determinants involved in interactions between IGFs, their receptors or their binding proteins, the ability to carry out such cross-linking studies with purified In-IGF-BP will be useful in examining these interactions.

Example 8

Use of In-IGF-BP in Biological Proliferation Assays

Figure 4:
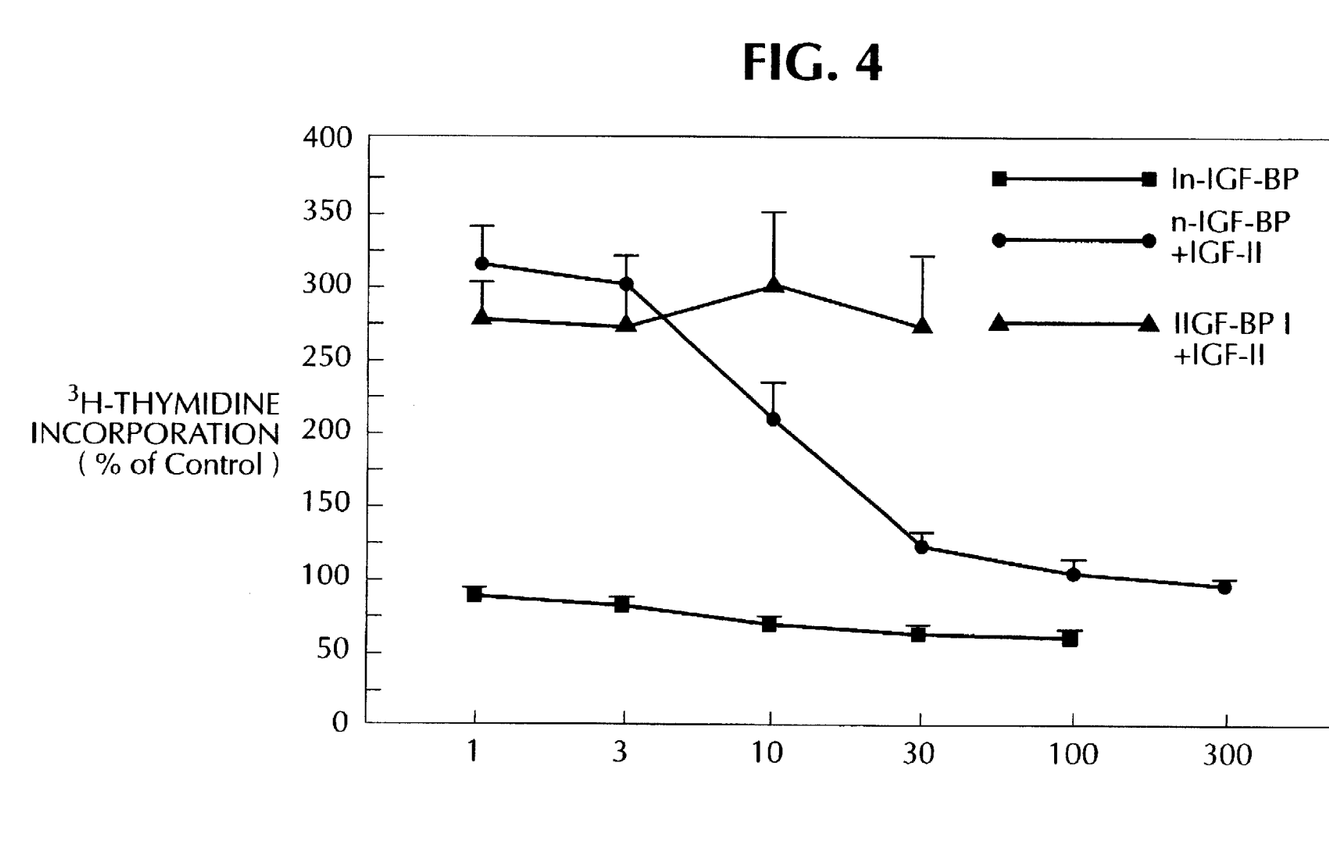
FIG. 4 shows the effect of In-IGF-BP or IGF-BP I on IGF-induced proliferation of chicken bone cells in serum free medium.
Figure 5:
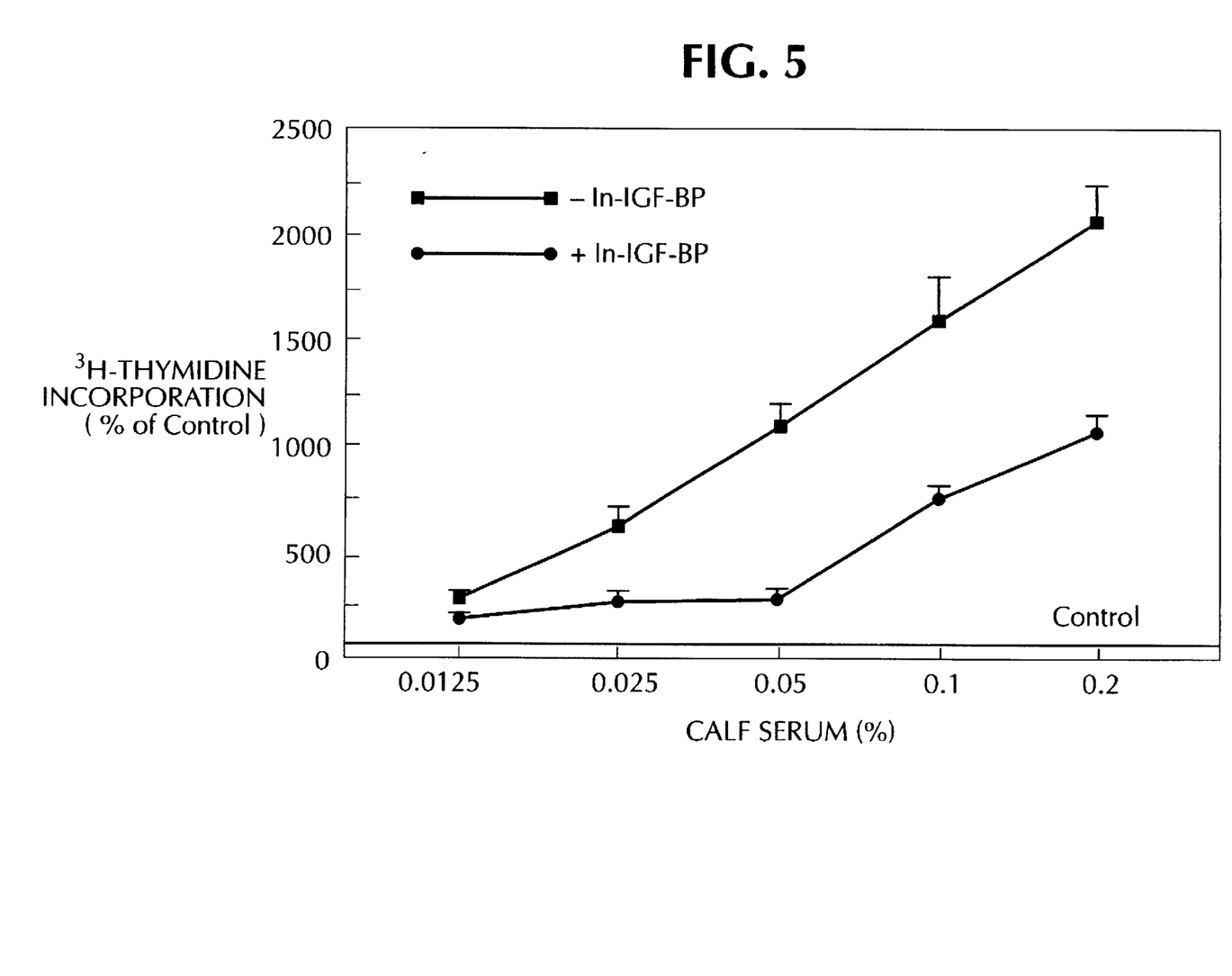
FIG. 5 shows the effect of 5 ng In-IGF-BP on serum-induced proliferation of MC3T3-E1 cells at various serum concentrations.

Mohan et al., Biochim. Biophys. Acta 884:234–242 (1986) describes an assay for IGF-mediated proliferation of bone cells in serum-free culture medium. The assay described in that article, which is hereby incorporated by reference, measures the incorporation of tritiated thymidine into trichloroacetic acid precipitable cellular material. Addition of 3 ng/ml IGF-II to chicken bone cells stimulated tritiated thyroidine incorporation by 2.2-fold over untreated cells. This stimulation of proliferation was inhibited in a dose dependent manner by the addition of In-IGF-BP but not by IGF-BP I (See FIG. 4). Additionally, In-IGF-BP inhibited serum-induced stimulation of proliferation of MC3T3-E1 cells when 5 ng In-IGF-BP was incubated with serum at room temperature for 60 minutes prior to the addition of the serum to the cells in serum free medium (See FIG. 5). These results indicate that this system provides another assay for In-IGF-BP and illustrate the ability of In-IGF-BP to inhibit proliferation of cells in response to purified IGFs or serum. Thus purified In-IGF-BP is useful in biological assays which examine the effects of certain growth factors on a variety of cell types.

Example 9

Quantitative Diagnostic Assay for IGF-I or IGF-II Using In-IGF-BP in Liquid Phase Competitive Binding Five nanograms of purified In-IGF-BP was incubated with 40,000 cpm of $^{125}$I-labeled IGF-I or IGF-II in the presence or absence of unlabelled competitor. IGF-I or IGF-II standards or sample containing unknown amounts of IGF were used as competitors. After 60 minutes of incubation at room temperature, In-IGF-BP-IGF complex was precipitated by adding polyethylene glycol in the presence of bovine gamma globulin as described in Example 5. After a 30 minute centrifugation at 1185× g an aliquot of the supernatant was counted in the gamma counter. A standard curve was set up with different concentrations of unlabelled IGF and the amount of IGF in the unknown sample was calculated using this standard curve. Thus, the amount of biologically active free IGFs are determinable by this assay which utilizes purified In-IGF-BP that has high affinity for IGFs.

Example 10

Inhibition of IGF-responsive Tumor Cells Proliferation by In-IGF-BP

TE85 human osteosarcoma cells produce abundant IGF-II in serum free culture and grow rapidly under serum free conditions, suggesting that IGF-II is an important autocrine mitogen for these tumor cells. Therefore, it might be possible to inhibit TE85 cell proliferation by exogenously adding purified In-IGF-BP under serum free conditions. Addition of In-IGF-BP at 100 ng/ml inhibited TE85 cell proliferation by 40-50% of untreated control cells. In addition, agents which increase intracellular cyclic AMP inhibited TE85 cell proliferation and this inhibition of cell proliferation by dibutyl cyclic AMP and other agents correlated positively with the level of In-IGF-BP in the conditioned medium. Based on these findings, we propose that In-IGF-BP is a potential therapeutic agent to inhibit cell proliferation in IGF responsive tumors. The inhibition of cell proliferation can be accomplished either by local administration of purified In-IGF-BP in the tumor areas or by treating individuals with IGF responsive tumors with agents which stimulate production of In-IGF-BP (e.g. Prostaglandin E2).

Example 11

Cloning and Sequencing of a Nucleic Acid Sequence Encoding In-IGF-BP

Polyadenylated RNA was isolated from TE89 human osteosarcoma cells by standard procedures. A cDNA library was prepared from this polyadenylated RNA, using the PHAGEMID™ cDNA vector system. (Invitrogen, San Diego, Calif.). A library of 10⁵ PHAGEMID™ cDNA clones was screened with a 14-met mixed oligonucleotide probe reflecting the amino terminal sequence of purified In-IGF-BP. Four positive clones were identified and the clone containing the longest insert was sequenced according to standard procedures. The complete nucleic acid sequence obtained and the deduced amino acid sequence for In-IGF-BP are shown in FIG. 1. The complete nucleic acid sequence encoding In-IGF-BP contains a long open reading frame of 774 nucleohides preceded by a 5' untranslated region of at least 400 bp. The deduced amino acid sequence of In-IGF-BP indicates a mature binding protein of 237 amino acids preceded by a hydrophobic 21 amino acid leader sequence. The deduced amino acid sequence predicts an amino acid composition and molecular weight in accord with those which are observed In-IGF-BP.

Example 12

Use of the Nucleotide Sequence Encoding In-IGF-BP In Studies of Physiological Distribution of Its Expression Gene expression studies are important means of understanding the physiological significance of particular proteins. For example, the spatial or temporal distribution of expression of a gene in a particular organism, or its expression in response to hormones or other agents can provide clues to the physiological role of the protein. In order to better understand the role of In-IGF-BP, studies were conducted of its expression in various tissues, and of its expression in response to parathyroid hormone (PTH), which is correlated with increased IGF-BP in elderly hip fracture patients. In either study, total RNA was isolated from cultured cells or tissues and was fractionated on a formaldehyde-agarose gel then transferred to a NYTRAN™ membrane. Cultured bone cells grown in the presence or absence of PTH were used in the PTH-effect study. The NYTRAN™ membranes were then hybridized with a radiolabelled nucleotide sequence encoding In-IGF-BP. A 2.1 kb RNA hybridized to the probe in a variety of cell types, indicating that In-IGF-BP is constitutively produced not only in bone cells, but in other cell types as well. In-IGF-BP expression is increased about 1.4-fold over control levels when PTH is added to bone cells in serum free medium, indicating that In-IGF-BP expression may be regulated by hormone signals.

Example 13

Preparation of Artificial Expression Systems and Host Cells

The cDNA sequence shown in FIG. 1 was inserted into the EcoR1 site of pSV328, which expresses cloned inserts using the simian virus 40 (SV40) early promoter. COS-1 cells were transfected with the In-IGF-BP expression vector by calcium phosphate method (Gorman, High efficiency transfer into mammalian cells: In; DNA cloning (Glover, DM), IRL Press, Oxford, Vol2: 143-190, 1985). The media conditioned by transfected cells was then assayed for In-IGF-BP activity and used for purification as described in Example 3.

Example 14

In-IGF-BP as a Diagnostic Agent

We found that the production of In-IGF-BP is increased by treatment of bone cells with parathyroid hormone (PTH). In vivo, In-IGF-BP level is elevated 4-6 fold in sera from elderly hip fracture patients who have elevated PTH. Thus, In-IGF-BP shows potential as a diagnostic marker for disease states such as osteoporosis. Accordingly, high serum In-IGF-BP is likely to indicate osteoporosis associated with secondary hyperparathyroidism. Also, high serum In-IGF-BP is a likely marker of low bone formation in different types of osteoporosis. Since In-IGF-BP inhibits cell proliferation in certain types of cancer cells, a low serum In-IGF-BP will likely be associated with some cancers. In-IGF-BP levels can be measured by a radioimmunoassay using antibodies directed against purified intact In-IGF-BP or synthetic fragments developed from the deduced amino acid sequence shown in FIG. 1 and purified In-IGF-BP as standard and tracer.

What is claimed is:

1. Isolated inhibitory insulin-like growth factor binding protein having an amino acid sequence identical to the amino acid sequence of FIG. 1 and having a molecular weight of approximately 25 kd as determined on an SDS gel under reducing conditions.

2. A method for modulating the effects of IGF upon bone cells, comprising the step of treating the bone cells with the In-IGF-BP of claim 1.

3. A method for diagnostically assaying clinical samples for IGD levels, comprising the steps of:
   (a) binding the In-IGF-BP of claim 1 to labelled IGF; and
   (b) competing the bound IGF away with liquid derived from a clinical sample.

* * * * *

UNITED STATES PATENT AND TRADEMARK OFFICE
CERTIFICATE OF CORRECTION

PATENT NO. : 5,693,754
DATED : December 2, 1997
INVENTOR(S) : David J. Baylink, et al.

It is certified that error appears in the above-identified patent and that said Letters Patent is hereby corrected as shown below:

In column 2, line 11, change "Proyon" to --Provoa--.

In column 2, line 25, change "Blochem." to --Biochem.--.

In column 3, line 50, change "(1939)" to --(1989)--.

In column 4, line 18, change "arc" to --are--.

In column 7, line 28, change "NAN3" to --NaN3--.

In column 7, line 43, change "H-55" to --H-35--.

In column 8, line 39, change "thyroidine" to --thymidine--.

In column 9, line 41, change "14-met" to -- 14-mer --.

In Claim 3, column 10, line 62, change "IGD" to -- IGF--.

Signed and Sealed this

Twenty-seventh Day of July, 1999

*Attest:*

Q. TODD DICKINSON

*Attesting Officer*   *Acting Commissioner of Patents and Trademarks*